US010492530B2

(12) United States Patent
Rogers et al.

(10) Patent No.: US 10,492,530 B2
(45) Date of Patent: Dec. 3, 2019

(54) TWO-WIRE AUTHENTICATION SYSTEM FOR AN AEROSOL DELIVERY DEVICE

(71) Applicant: RAI Strategic Holdings, Inc., Winston-Salem, NC (US)

(72) Inventors: James W. Rogers, Winston-Salem, NC (US); Percy Phillips, Pfafftown, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 460 days.

(21) Appl. No.: 15/352,078

(22) Filed: Nov. 15, 2016

(65) Prior Publication Data

US 2018/0132530 A1 May 17, 2018

(51) Int. Cl.

*A61M 15/06* (2006.01)
*A24F 47/00* (2006.01)
*H05B 1/02* (2006.01)

(52) U.S. Cl.

CPC ......... *A24F 47/008* (2013.01); *H05B 1/0244* (2013.01); *H05B 2203/021* (2013.01)

(58) Field of Classification Search

None

See application file for complete search history.

(56) References Cited

U.S. PATENT DOCUMENTS 1,771,366 A 7/1930 Wyss et al.
2,057,353 A 10/1936 Whittemore, Jr.
2,104,266 A 1/1938 McCormick
3,200,819 A 8/1965 Gilbert
4,284,089 A 8/1981 Ray
4,303,083 A 12/1981 Burruss, Jr.
4,735,217 A 4/1988 Gerth et al.
(Continued)

FOREIGN PATENT DOCUMENTS

AU 276250 7/1965
CA 2 641 869 5/2010
(Continued)

OTHER PUBLICATIONS

International Search Report dated Feb. 5, 2018 in International Application No. PCT/IB2017/057136 filed Nov. 15, 2017.

*Primary Examiner* — Thor S Campbell

(74) *Attorney, Agent, or Firm* — Womble Bond Dickinson (US) LLP

(57) ABSTRACT

An aerosol delivery device is provided that includes a cartridge coupled with a control body. The cartridge is equipped with a heating element, an authentication device and a second switching circuit. The control body includes a first switching circuit and is configured to exchange authentication signals with the authentication device to authenticate the cartridge for use with the control body and, only in instances in which the cartridge is authenticated, direct power to the heating element. The control body and the cartridge include respectively a two-wire electrical connector and a corresponding two-wire electrical connector coupled with one another, and across which the authentication signals are exchanged and the power is directed. The first switching circuit is coupled with the second switching circuit to form switching circuitry configured to manage the authentication signals and the power across the two-wire electrical connector.

18 Claims, 5 Drawing Sheets

(56) References Cited

U.S. PATENT DOCUMENTS 4,848,374 A 7/1989 Chard et al.
4,907,606 A 3/1990 Lilja et al.
4,922,901 A 5/1990 Brooks et al.
4,945,931 A 8/1990 Gori
4,947,874 A 8/1990 Brooks et al.
4,947,875 A 8/1990 Brooks et al.
4,986,286 A 1/1991 Roberts et al.
5,019,122 A 5/1991 Clearman et al.
5,042,510 A 8/1991 Curtiss et al.
5,060,671 A 10/1991 Counts et al.
5,093,894 A 3/1992 Deevi et al.
5,144,962 A 9/1992 Counts et al.
5,249,586 A 10/1993 Morgan et al.
5,261,424 A 11/1993 Sprinkel, Jr.
5,322,075 A 6/1994 Deevi et al.
5,353,813 A 10/1994 Deevi et al.
5,369,723 A 11/1994 Counts et al.
5,372,148 A 12/1994 McCafferty et al.
5,388,574 A 2/1995 Ingebrethsen et al.
5,408,574 A 4/1995 Deevi et al.
5,468,936 A 11/1995 Deevi et al.
5,498,850 A 3/1996 Das
5,515,842 A 5/1996 Ramseyer et al.
5,530,225 A 6/1996 Hajaligol
5,564,442 A 10/1996 MacDonald et al.
5,649,554 A 7/1997 Sprinkel et al.
5,666,977 A 9/1997 Higgins et al.
5,687,746 A 11/1997 Rose et al.
5,726,421 A 3/1998 Fleischhauer et al.
5,727,571 A 3/1998 Meiring et al.
5,743,251 A 4/1998 Howell et al.
5,799,663 A 9/1998 Gross et al.
5,819,756 A 10/1998 Mielordt
5,865,185 A 2/1999 Collins et al.
5,865,186 A 2/1999 Volsey, II
5,878,752 A 3/1999 Adams et al.
5,894,841 A 4/1999 Voges
5,934,289 A 8/1999 Watkins et al.
5,954,979 A 9/1999 Counts et al.
5,967,148 A 10/1999 Harris et al.
6,040,560 A 3/2000 Fleischhauer et al.
6,053,176 A 4/2000 Adams et al.
6,089,857 A 7/2000 Matsuura et al.
6,095,153 A 8/2000 Kessler et al.
6,125,853 A 10/2000 Susa et al.
6,155,268 A 12/2000 Takeuchi
6,164,287 A 12/2000 White
6,196,218 B1 3/2001 Voges
6,196,219 B1 3/2001 Hess et al.
6,598,607 B2 7/2003 Adiga et al.
6,601,776 B1 8/2003 Oljaca et al.
6,615,840 B1 9/2003 Fournier et al.
6,688,313 B2 2/2004 Wrenn et al.
6,772,756 B2 8/2004 Shayan
6,803,545 B2 10/2004 Blake et al.
6,854,461 B2 2/2005 Nichols
6,854,470 B1 2/2005 Pu
7,117,867 B2 10/2006 Cox et al.
7,293,565 B2 11/2007 Griffin et al.
7,513,253 B2 4/2009 Kobayashi et al.
7,775,459 B2 8/2010 Martens, III et al.
7,832,410 B2 11/2010 Hon
7,845,359 B2 12/2010 Montaser
7,896,006 B2 3/2011 Hamano et al.
8,127,772 B2 3/2012 Montaser
8,314,591 B2 11/2012 Terry et al.
8,365,742 B2 2/2013 Hon
8,402,976 B2 3/2013 Fernando et al.
8,499,766 B1 8/2013 Newton
8,528,569 B1 9/2013 Newton
8,550,069 B2 10/2013 Alelov
8,833,364 B2 * 9/2014 Buchberger ......... A61M 11/041
128/202.21
8,851,081 B2 10/2014 Fernando et al.
8,897,628 B2 * 11/2014 Conley ................. A24F 47/008
392/386
9,864,947 B1 * 1/2018 Sur ....................... A24F 47/008
2002/0146242 A1 10/2002 Vieira
2003/0226837 A1 12/2003 Blake et al.
2004/0118401 A1 6/2004 Smith et al.
2004/0129280 A1 7/2004 Woodson et al.
2004/0200488 A1 10/2004 Felter et al.
2004/0226568 A1 11/2004 Takeuchi et al.
2005/0016550 A1 1/2005 Katase
2006/0016453 A1 1/2006 Kim
2006/0196518 A1 9/2006 Hon
2007/0074734 A1 4/2007 Braunshteyn et al.
2007/0102013 A1 5/2007 Adams et al.
2007/0215167 A1 9/2007 Crooks et al.
2008/0085103 A1 4/2008 Beland et al.
2008/0092912 A1 4/2008 Robinson et al.
2008/0257367 A1 10/2008 Paterno et al.
2008/0276947 A1 11/2008 Martzel
2008/0302374 A1 12/2008 Wengert et al.
2009/0095311 A1 4/2009 Hon
2009/0095312 A1 4/2009 Herbrich et al.
2009/0126745 A1 5/2009 Hon
2009/0188490 A1 7/2009 Hon
2009/0230117 A1 9/2009 Fernando et al.
2009/0272379 A1 11/2009 Thorens et al.
2009/0283103 A1 11/2009 Nielsen et al.
2009/0320863 A1 12/2009 Fernando et al.
2010/0043809 A1 2/2010 Magnon
2010/0083959 A1 4/2010 Siller
2010/0200006 A1 8/2010 Robinson et al.
2010/0229881 A1 9/2010 Hearn
2010/0242974 A1 9/2010 Pan
2010/0307518 A1 12/2010 Wang
2010/0313901 A1 12/2010 Fernando et al.
2011/0005535 A1 1/2011 Xiu
2011/0011396 A1 1/2011 Fang
2011/0036363 A1 2/2011 Urtsev et al.
2011/0036365 A1 2/2011 Chong et al.
2011/0094523 A1 4/2011 Thorens et al.
2011/0126848 A1 6/2011 Zuber et al.
2011/0155153 A1 6/2011 Thorens et al.
2011/0155718 A1 6/2011 Greim et al.
2011/0168194 A1 7/2011 Hon
2011/0265806 A1 11/2011 Alarcon et al.
2011/0309157 A1 12/2011 Yang et al.
2012/0042885 A1 2/2012 Stone et al.
2012/0060853 A1 3/2012 Robinson et al.
2012/0111347 A1 5/2012 Hon
2012/0132643 A1 5/2012 Choi et al.
2012/0227752 A1 9/2012 Alelov
2012/0231464 A1 9/2012 Yu et al.
2012/0260927 A1 10/2012 Liu
2012/0279512 A1 11/2012 Hon
2012/0318882 A1 12/2012 Abehasera
2013/0037041 A1 2/2013 Worm et al.
2013/0056013 A1 3/2013 Terry et al.
2013/0081625 A1 4/2013 Rustad et al.
2013/0081642 A1 4/2013 Safari
2013/0192619 A1 8/2013 Tucker et al.
2013/0255702 A1 10/2013 Griffith, Jr. et al.
2013/0306084 A1 11/2013 Flick
2013/0319439 A1 12/2013 Gorelick et al.
2013/0340750 A1 12/2013 Thorens et al.
2013/0340775 A1 12/2013 Juster et al.
2014/0000638 A1 1/2014 Sebastian et al.
2014/0060554 A1 3/2014 Collett et al.
2014/0060555 A1 3/2014 Chang et al.
2014/0096781 A1 * 4/2014 Sears .................... A24F 47/008
131/328
2014/0096782 A1 * 4/2014 Ampolini .............. A24F 47/008
131/328
2014/0109921 A1 4/2014 Chen
2014/0157583 A1 6/2014 Ward et al.
2014/0209105 A1 7/2014 Sears et al.
2014/0253144 A1 9/2014 Novak et al.
2014/0261408 A1 9/2014 DePiano et al.
2014/0261486 A1 9/2014 Potter et al.
2014/0261487 A1 9/2014 Chapman et al.

(56) References Cited

U.S. PATENT DOCUMENTS

| | | | | |
|---|---|---|---|---|
| 2014/0261495 | A1 | 9/2014 | Novak et al. | |
| 2014/0270727 | A1* | 9/2014 | Ampolini | A24F 47/008 392/387 |
| 2014/0270729 | A1* | 9/2014 | DePiano | A24F 47/008 392/397 |
| 2014/0270730 | A1* | 9/2014 | DePiano | A24F 47/008 392/404 |
| 2014/0345631 | A1 | 11/2014 | Bowen et al. | |
| 2015/0007838 | A1 | 1/2015 | Fernando et al. | |
| 2015/0053217 | A1 | 2/2015 | Steingraber et al. | |
| 2015/0223522 | A1* | 8/2015 | Ampolini | A24F 47/008 131/328 |
| 2015/0359263 | A1* | 12/2015 | Bellinger | H05B 1/0244 392/394 |
| 2016/0037826 | A1 | 2/2016 | Hearn et al. | |
| 2016/0089508 | A1* | 3/2016 | Smith | A61M 15/06 128/200.16 |
| 2016/0174610 | A1* | 6/2016 | Kuczaj | A24F 47/008 131/328 |
| 2016/0309788 | A1* | 10/2016 | Hawes | A24F 47/008 |
| 2017/0064997 | A1* | 3/2017 | Murison | A24F 15/12 |
| 2017/0181471 | A1* | 6/2017 | Phillips | H02J 7/0029 |
| 2017/0231277 | A1* | 8/2017 | Mironov | A24F 47/008 392/404 |
| 2017/0231278 | A1* | 8/2017 | Mironov et al. | A24F 47/008 392/390 |
| 2018/0153219 | A1* | 6/2018 | Verleur | A24F 47/008 |
| 2018/0303160 | A1* | 10/2018 | Davis | A24F 47/008 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2016/156609 | 10/2016 |

* cited by examiner

TWO-WIRE AUTHENTICATION SYSTEM FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, it may be desirable to provide a two-wire authentication system for authenticating and directing power within an aerosol delivery device.

BRIEF SUMMARY

The present disclosure relates to aerosol delivery devices, methods of forming such devices, and elements of such devices. The present disclosure includes, without limitation, the following example implementations. In some example implementations, an aerosol delivery device is provided. The aerosol delivery device may comprise a cartridge and a control body coupled therewith. The cartridge is equipped with a heating element and an authentication device, and contains an aerosol precursor composition. The control body is configured to exchange authentication signals with the authentication device to authenticate the cartridge for use with the control body. Only in instances in which the cartridge is authenticated, the control body is configured to direct power to the heating element to activate and vaporize components of the aerosol precursor composition.

The control body and the cartridge include respectively a two-wire electrical connector and a corresponding two-wire electrical connector coupled with one another, and across which the authentication signals are exchanged and the power is directed. The control body and the cartridge further include respectively a first switching circuit and a second switching circuit. The first switching circuit is coupled with the second switching circuit to form switching circuitry configured to manage the authentication signals and the power across the two-wire electrical connector.

In some example implementations of the aerosol delivery device of the preceding or any subsequent example implementation, or any combination thereof, the predetermined threshold voltage is 2.5 volts.

In some example implementations of the aerosol delivery device of any preceding or any subsequent example implementation, or any combination thereof, the switching circuitry being configured to manage the authentication signals and the power across the two-wire electrical connector includes being configured to receive and forward a signal to the authentication device as one of the authentication signals in an instance in which the signal has a voltage level at or below the predetermined threshold voltage.

In some example implementations of the aerosol delivery device of any preceding or any subsequent example implementation, or any combination thereof, the switching circuitry being configured to receive and forward the signal includes being configured to receive a plurality of signals and forward signals of the plurality of signals to the authentication device as authentication signals until a signal of the plurality of signals has a voltage level above the predetermined threshold voltage.

In some example implementations of the aerosol delivery device of any preceding or any subsequent example implementation, or any combination thereof, the switching circuitry being configured to manage the authentication signals and the power across the two-wire electrical connector includes being configured to receive and forward a signal to the heating element as power directed thereto in an instance in which the signal has a voltage level above the predetermined threshold voltage.

In some example implementations of the aerosol delivery device of any preceding or any subsequent example implementation, or any combination thereof, the authentication signals and the power are formatted as pulse width modulation (PWM) signals having respectively a first frequency and a second frequency, the first frequency being at least two times larger than the second frequency.

In some example implementations of the aerosol delivery device of any preceding or any subsequent example implementation, or any combination thereof, . . . .

In some example implementations of the aerosol delivery device of any preceding or any subsequent example implementation, or any combination thereof, the switching circuitry being configured to manage the authentication signals and the power across the two-wire electrical connector includes the switching circuitry being configured to switch a PWM signal having the first frequency across the two-wire electrical connector between pulses of a PWM signal having the second frequency.

In some example implementations of the aerosol delivery device of any preceding or any subsequent example implementation, or any combination thereof, the control component being configured to direct power to the heating element includes being configured to direct power to the heating element in response to a flow of air through at least a portion of the aerosol delivery device, the air being combinable with vapor formed by vaporization of components of the aerosol precursor composition to form an aerosol.

In some example implementations, a control body coupled or coupleable with a cartridge to form an aerosol delivery device is provided. The cartridge may be equipped with a heating element and an authentication device, and contain an aerosol precursor composition. The control body may include a control component configured to exchange authentication signals with the authentication device to authenticate the cartridge for use with the control body, and only in instances in which the cartridge is authenticated, direct power to the heating element to activate and vaporize components of the aerosol precursor composition. The control body may also include a two-wire electrical connector coupled with a corresponding two-wire electrical connector of the cartridge when the control body is coupled with the cartridge, and across which the authentication signals are exchanged and the power is directed. The control body may also include a first switching circuit coupled with a second switching circuit of the cartridge when the control body is coupled with the cartridge. The first switching circuit is coupled with the second switching circuit to form switching circuitry configured to manage the authentication signals and the power across the two-wire electrical connector.

In some example implementations of the control body of the preceding or any subsequent example implementation, or any combination thereof, the authentication signals across the two-wire electrical connector have a voltage level at or below a predetermined threshold voltage, and the power across the two-wire electrical connector has a voltage level above the predetermined threshold voltage.

In some example implementations of the control body of any preceding or any subsequent example implementation, or any combination thereof, the predetermined threshold voltage is 2.5 volts.

In some example implementations of the control body of any preceding or any subsequent example implementation, or any combination thereof, the switching circuitry being configured to manage the authentication signals and the power across the two-wire electrical connector includes being configured to receive and forward a signal to the authentication device as one of the authentication signals in an instance in which the signal has a voltage level at or below the predetermined threshold voltage.

In some example implementations of the control body of any preceding or any subsequent example implementation, or any combination thereof, the switching circuitry being configured to receive and forward the signal includes being configured to receive a plurality of signals and forward signals of the plurality of signals to the authentication device as authentication signals until a signal of the plurality of signals has a voltage level above the predetermined threshold voltage.

In some example implementations of the control body of any preceding or any subsequent example implementation, or any combination thereof, the switching circuitry being configured to manage the authentication signals and the power across the two-wire electrical connector includes being configured to receive and forward a signal to the heating element as power directed thereto in an instance in which the signal has a voltage level above the predetermined threshold voltage.

In some example implementations of the control body of any preceding or any subsequent example implementation, or any combination thereof, the authentication signals and the power are formatted as pulse width modulation (PWM) signals having respectively a first frequency and a second frequency, the first frequency being at least two times larger than the second frequency.

In some example implementations of the control body of any preceding or any subsequent example implementation, or any combination thereof, the switching circuitry being configured to manage the authentication signals and the power across the two-wire electrical connector includes the switching circuitry being configured to switch a PWM signal having the first frequency across the two-wire electrical connector between pulses of a PWM signal having the second frequency.

In some example implementations of the control body of any preceding or any subsequent example implementation, or any combination thereof, the control component being configured to direct power to the heating element includes being configured to direct power to the heating element in response to a flow of air through at least a portion of the aerosol delivery device, the air being combinable with vapor formed by vaporization of components of the aerosol precursor composition to form an aerosol.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
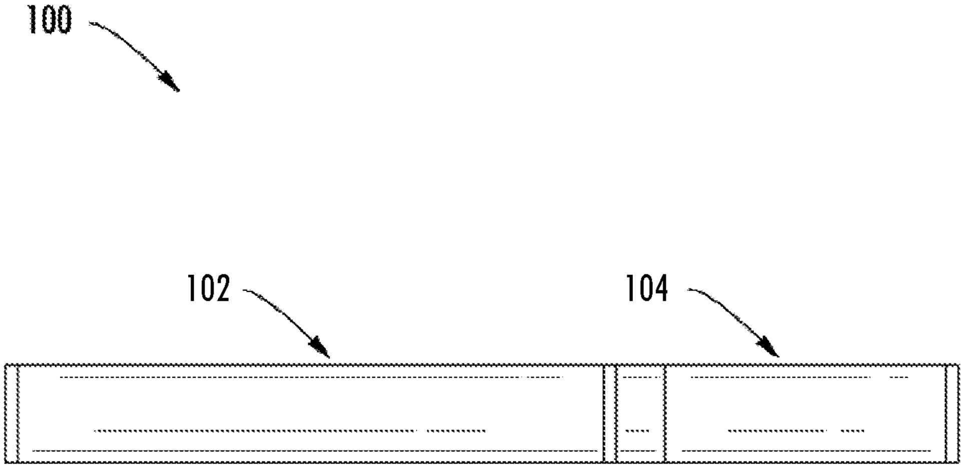
FIG. 1 illustrates a side view of an aerosol delivery device including a cartridge coupled to a control body according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery, thin film solid state battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. Further, in some example implementations, the cartridge may comprise a single-use cartridge, as disclosed in U.S. Pat. No. 8,910,639 to Chang et al., which is incorporated herein by reference in its entirety.

Figure 2:
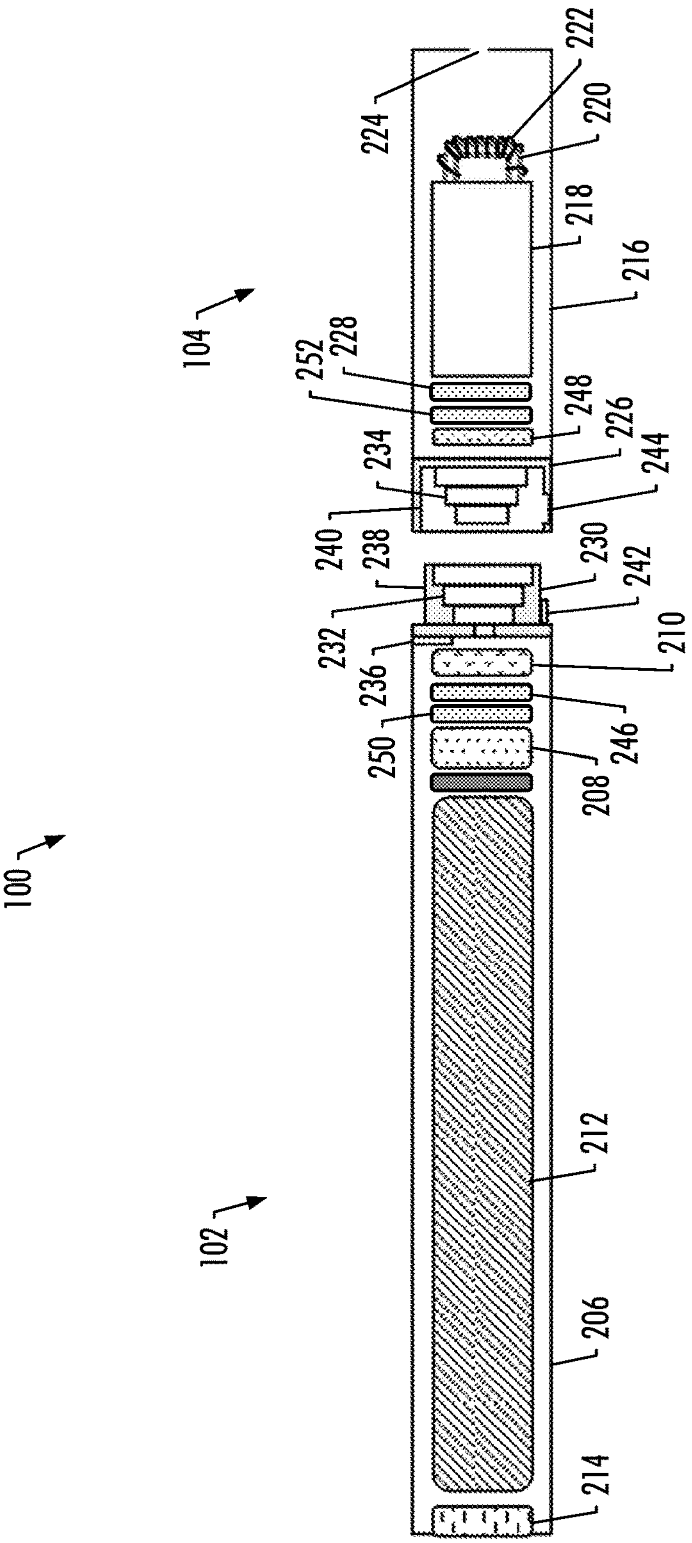
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include one or more of each of a number of electronic components, such as a control component 208 (e.g., a microprocessor, individually or as part of a microcontroller), a flow sensor 210, a power source 212 and/or light-emitting diode (LED) 214, and such components can be variably aligned. The power source may include, for example, a battery (single-use or rechargeable), solid-state battery, thin-film solid-state battery, supercapacitor or the like, or some combination thereof. Some examples of a suitable power source are provided in U.S. patent application Ser. No. 14/918,926 to Sur et al., filed Oct. 21, 2015, which is incorporated by reference. The LED may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

The cartridge 104 can be formed of a cartridge shell 216 enclosing a reservoir 218 configured to retain the aerosol precursor composition, and including a heater 220 (sometimes referred to as a heating element). As shown, in some examples, the reservoir may be in fluid communication with a liquid transport element 222 adapted to wick or otherwise transport an aerosol precursor composition stored in the reservoir housing to the heater. In some example, a valve may be positioned between the reservoir and heater, and configured to control an amount of aerosol precursor composition passed or delivered from the reservoir to the heater. In various configurations, the structure including at least the shell, reservoir and heater may be referred to as a tank; and accordingly, the terms "cartridge," "tank" and the like may be used interchangeably to refer to a shell or other housing enclosing a reservoir for aerosol precursor composition, and including a heater.

Various examples of materials configured to produce heat when electrical current is applied therethrough may be employed to form the heater 220. The heater in these examples may be a resistive heating element such as a wire coil, micro heater or the like. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104.

The cartridge 104 also may include one or more electronic components, which may include an integrated circuit, a memory component, a sensor, or the like. The electronic components may be adapted to communicate with the control component 208 and/or with an external device by wired or wireless means. The electronic components may be positioned anywhere within the cartridge or a base 226 thereof.

As explained in greater detail below, for example, the electronic components of the cartridge 104 may include an authentication device 228 to deter or prevent counterfeit cartridges from being used with the control body 102. Examples of suitable authentication devices include the bq26150 authentication device from Texas Instruments, the ATSHA204 and ATSHA204A authentication devices from Atmel Corporation, and the like. Although not separately shown, an additional memory unit associated with the authentication device may be used to store a depletion amount of the cartridge unit, as well as to store other programmable features and information associated with the cartridge unit.

The control component 208 may be configured to communicate with the authentication device 228 to authenticate the cartridge 104 for use with the control body 102. This authentication may be initiated and carried out in a number of different manners. In some examples, the control component may be configured to communicate with the authentication device at the initiation of every puff on the device 100 to validate the cartridge as being a legitimate device for use with the control body. An error condition may result in instances in which the cartridge is not authorized, and this error condition may be indicated by one or more visual, audio or haptic indicators. Otherwise, the control component may permit the puff to continue in instances in which the cartridge is authorized, which may include the control component causing the heater 220 to activate and vaporize aerosol precursor composition. More information regarding authentication according to aspects of the present disclosure may be found in U.S. Pat. App. Pub. No. 2014/0270727 to Ampolini et al., which is incorporated herein by reference.

Although electronic components such as the control component 208 and flow sensor 210 are illustrated separately, it is understood that various electronic components may be combined on an electronic printed circuit board (PCB) that supports and electrically connects the electronic components. Further, the PCB may be positioned horizontally relative the illustration of FIG. 1 in that the PCB can be lengthwise parallel to the central axis of the control body. In some examples, one or more electronic components may comprise their own respective PCBs or other base elements to which they can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 226 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 220 in the cartridge. Further, the control body shell 206 can include an air intake 236, which may be a notch in the shell where it connects to the coupler that allows for passage of ambient air around the coupler and into the shell where it then passes through the cavity of the coupler and into the cartridge through the projection.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 226. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 222. The liquid transport element can transport the aerosol precursor composition stored in the reservoir via capillary action to the heater 220 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 220 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 226. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection and under-voltage lock out. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the flow sensor 210 or another sensor or detector for control of supply of electric power to the heater 220 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. Pat. App. Pub. No. 2015/0257445 to Henry et al., all of which are incorporated herein by reference.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. App. Pub. No. 2014/0209105 to Sears et al., which is incorporated herein by reference.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al., and U.S. patent application Ser. No. 15/222,615 to Watson et al., filed Jul. 28, 2016, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. App. Pub. No. 2015/0216233 to Sears et al., all of which are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

As indicated above, the control component 208 includes a number of electronic components, and in some examples may be formed of a PCB. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated herein by reference. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

The control component 208 may be configured to control one or more functional elements of the aerosol delivery device 100 in different states of the device. In examples in which the aerosol delivery device has a housing formed of separable bodies, the aerosol delivery device, and more particularly the control component 102, may be in the standby mode when the control component is uncoupled with the cartridge 104. In examples of either a unitary or separable housing, the aerosol delivery device may be in the standby mode between puffs when the control component is coupled with the cartridge. Similarly, in examples of either a unitary or separable housing, when the user draws on the device and the flow sensor 210 detects airflow, the aerosol delivery device may be placed in the active mode during which the control component may direct power from the power source 212 to power the heater 220 (heating element) and thereby control the heater to activate and vaporize components of the aerosol precursor composition.

As previously indicated, in some implementations, the control component 208 may be configured to communicate with the authentication device 228 to authenticate the cartridge 104 for use with the control body 102. In particular, the control component may be configured to exchange authentication signals with the authentication device to authenticate the cartridge for use with the control body and, only in instances in which the cartridge is authenticated, direct power to the heating element 220 to activate and vaporize components of the aerosol precursor composition. The control component may be configured to direct power to the heating element in response to a flow of air through at least a portion of the aerosol delivery device 100. In these implementations, the control body and cartridge may be coupled to one another and configured to exchange data (e.g., authentication data) and power therebetween using a two-wire authentication system. This configuration provides flexibility to use the control body or cartridge with other generic cartridges or control bodies, respectively, that have similar two-wire authentication systems.

As shown in FIG. 2, the control body 102 may include a two-wire electrical connector 246, and the cartridge 104 may include a corresponding two-wire electrical 248. The two-wire electrical connectors are coupled when the control body is coupled with the cartridge. As such, the authentication signals are exchanged, and the power is directed, across the coupled two-wire electrical connectors. Further, the control body may include a first switching circuit 250, and the cartridge may include a second switching circuit 252. Similarly, the first and second switching circuits are coupled when the control body is coupled with the cartridge. The first and second switching circuits may be coupled to form switching circuitry configured to manage exchange of the authentication signals and direction of the power across the two-wire electrical connectors.

In some examples, the authentication signals and the power are formatted as pulse width modulation (PWM) signals that have a first frequency and a second frequency, respectively. In these examples, the first frequency is at least two times larger than the second frequency. To manage the authentication signals and the power across the two-wire electrical connector, the switching circuitry (including first and second switching circuits 250, 252) is configured to switch a PWM signal having the first frequency across the two-wire electrical connectors 246, 248 between pulses of a PWM signal having the second frequency. In some examples, the first switching circuit may be or include a high-side switch operatively coupled to a bus transceiver in which the high-side switch is configured to receive and switch the PWM signal across the two-wire electrical connectors.

In some implementations, the authentication signals exchanged across the two-wire electrical connectors 246, 248 have a voltage level at or below a predetermined threshold voltage, and the power across the two-wire electrical connectors has a voltage level above the predetermined threshold voltage. In one implementation, the predetermined threshold voltage is 2.5 volts. For example, in an instance in which a signal has a voltage level above the predetermined threshold voltage, the switching circuitry (including first and second switching circuits 250, 252) is configured to receive and forward the signal to the heating element 220, as power directed thereto. In some examples, the predetermined threshold voltage corresponds to a nominal voltage of the power source 212.

Alternatively, in an instance in which a signal has a voltage level at or below the predetermined threshold voltage, the switching circuitry (including first and second switching circuits 250, 252) is configured to receive and forward the signal to the authentication device 228 as one of the authentication signals. In some examples, the switching circuitry is configured to receive a plurality of signals and forward the signals of the plurality of signals to the authentication device as authentication signals. In these examples implementations, the plurality of signals are forwarded until a signal of the plurality of signals has a voltage level above the predetermined threshold voltage.

Figure 3:
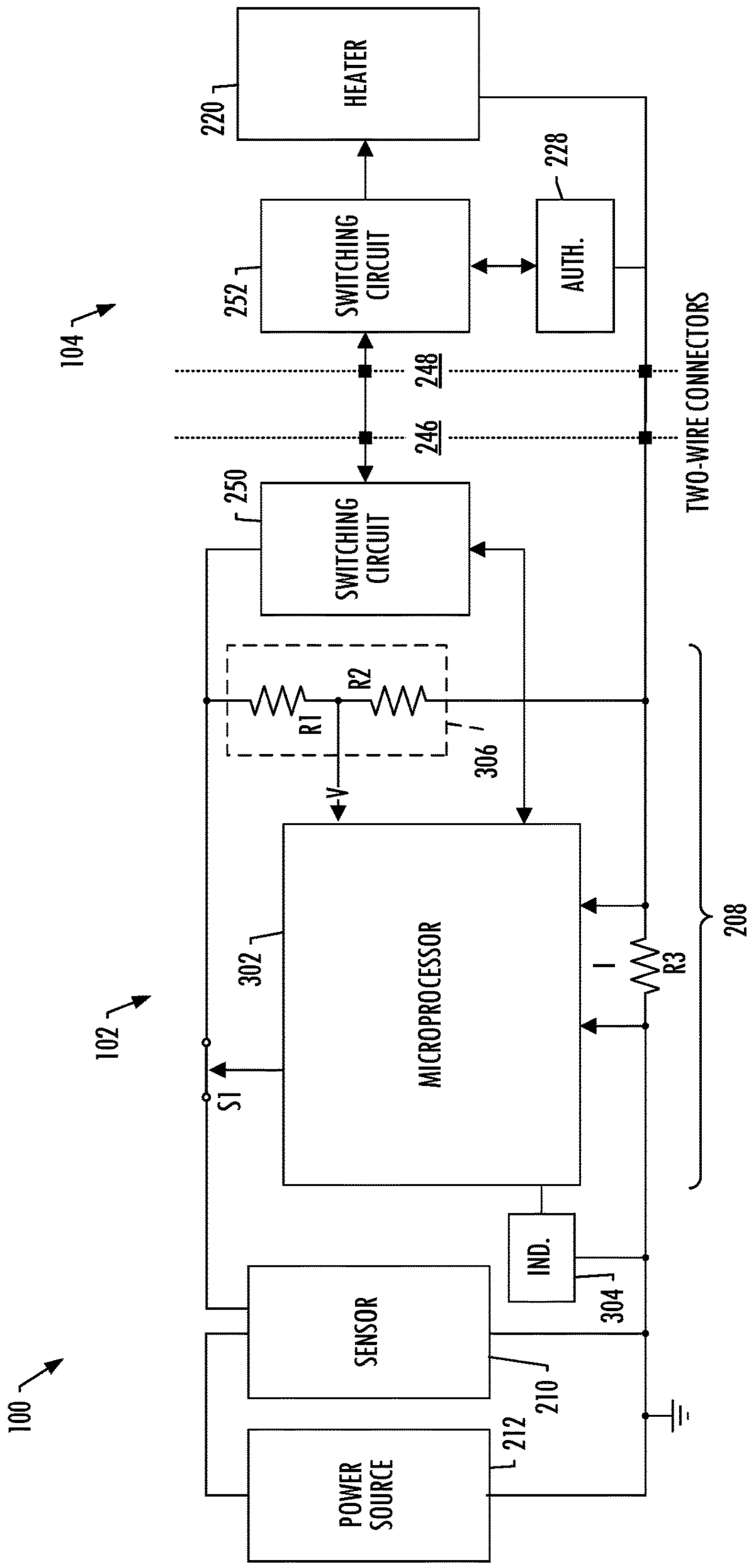
FIG. 3 illustrates various elements of a control body and cartridge of the aerosol delivery device, according to various example implementations.

FIG. 3 more particularly illustrates various interconnected electronic components of the control body 102 and cartridge 104, according to various example implementations. As shown, the control component 208 may include a microprocessor 302 and a number of other electrical components, such as resistors, capacitors, switches and the like, which may be coupled together and with the power source 212 and heater 220 via conductors such as wires, traces or the like to form an electrical circuit. In some examples, the heater may include a communication terminal for communicating data such as the puff count.

In accordance with example implementations of the present disclosure, the microprocessor 302 may be configured to perform a number of control operations. In the active mode, for example, the microprocessor may be configured to direct power from the power source 212 (e.g., directly or through the flow sensor 210) to turn the heater 222 on and thereby control the heater to activate and vaporize components of the aerosol precursor composition. This may include, for example, a switch S1 between the power source and the heater, which the microprocessor may operate in a closed state, as shown in FIG. 3. In some examples, the microprocessor may also control operation of at least one other functional element. One example of a suitable functional element may be an indicator 304 such as a visual, audio or haptic indicator.

In some examples, power delivery from the power source 212 may vary according to a power control mechanism, which may include the microprocessor 302 being configured to measure the voltage at a positive terminal of the heater 220 and control power to the heater based thereon. The voltage at the positive terminal may correspond to a positive heater voltage. The microprocessor may operate on the actual voltage, or an analog-to-digital converter (ADC) may be included to convert the actual voltage to a digital equivalent. In some examples, the control component 208 may include a voltage divider 306 with resistors R1 and R2, which may be configured to reduce the voltage to the microprocessor.

Figure 4:
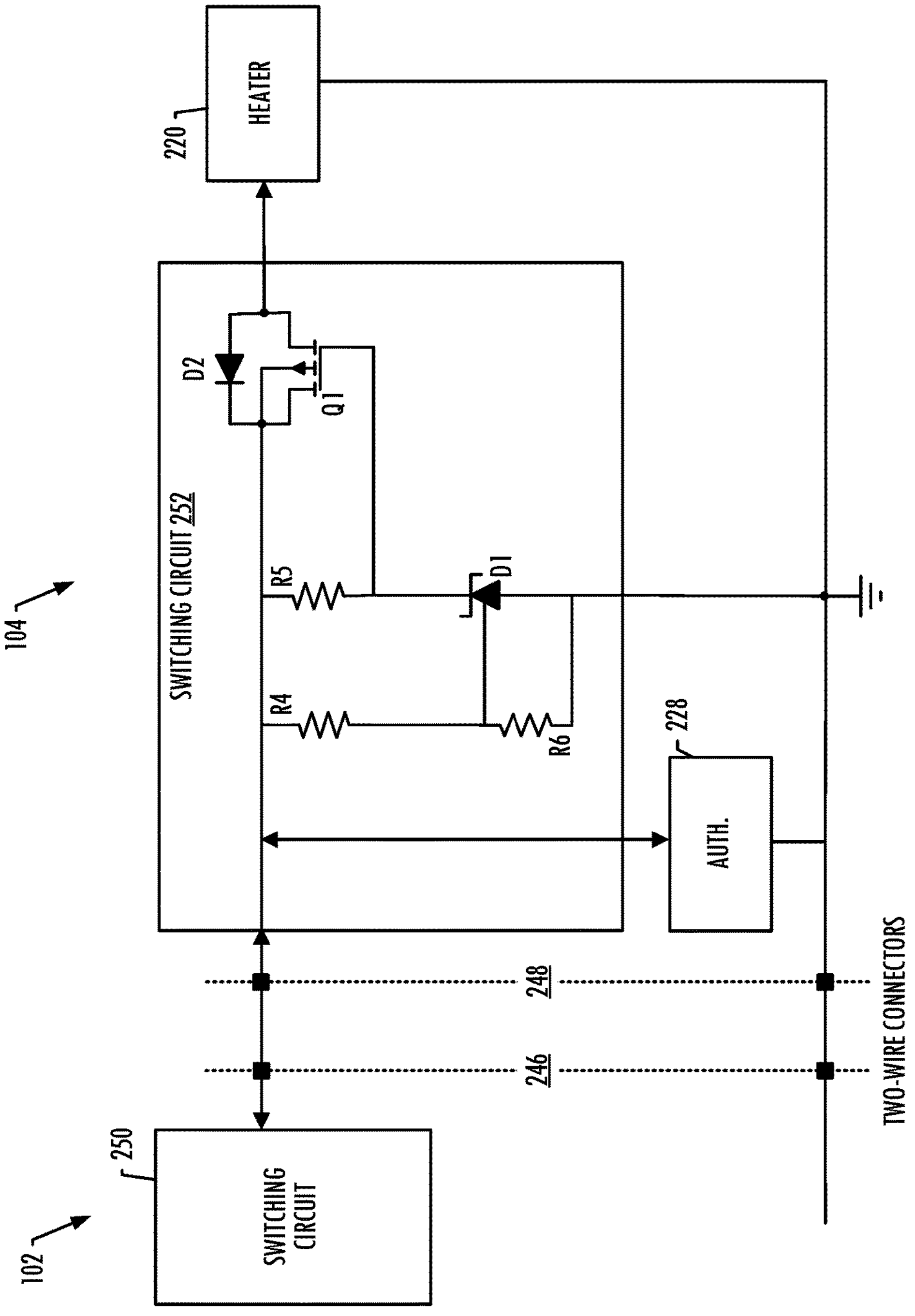
FIGS. 4 and 5 illustrate suitable switching circuits of the control body and cartridge of FIGS. 1, 2 and 3, accordingly to various example implementations.
Figure 5:
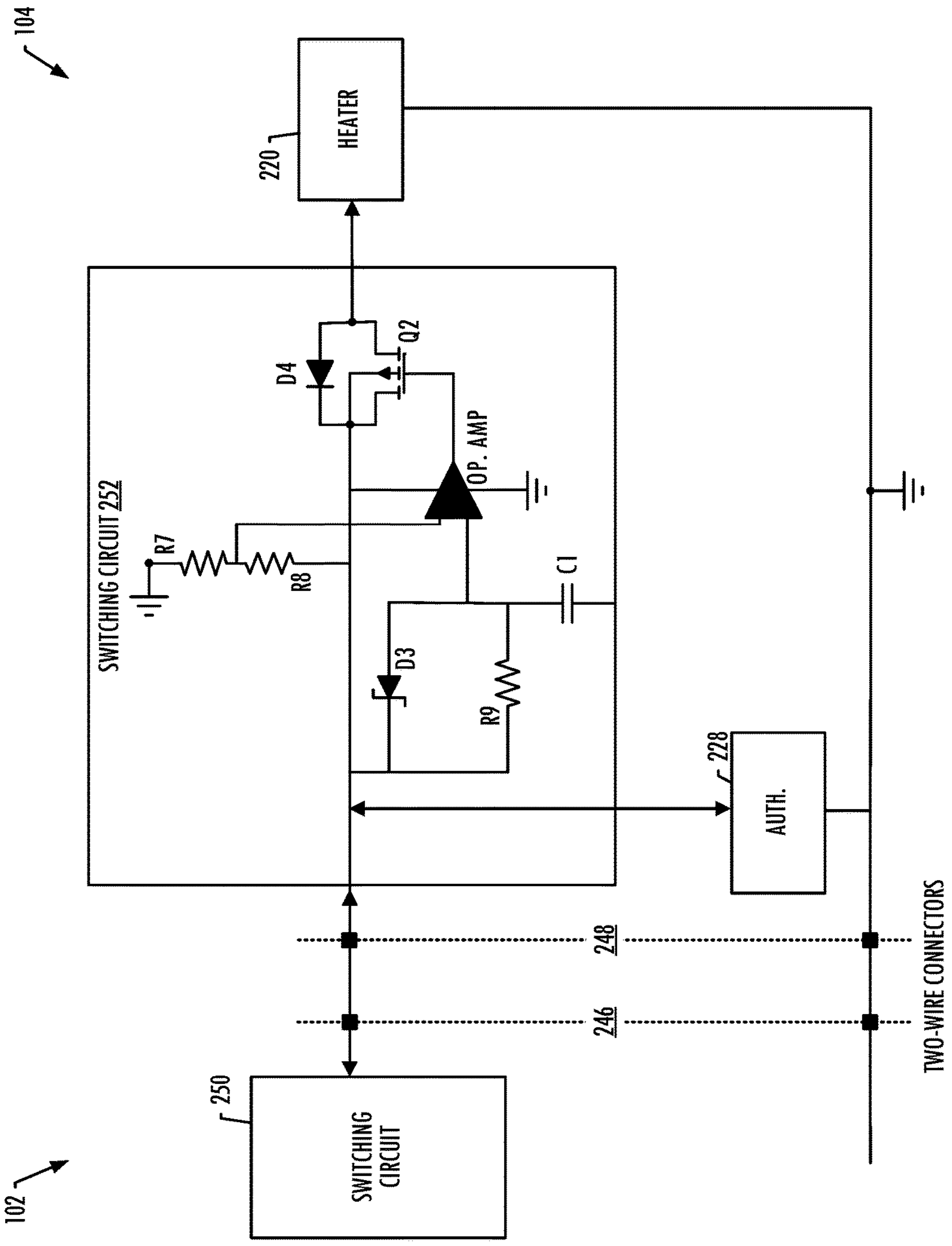

FIGS. 4 and 5 more particularly illustrate suitable examples of the switching circuitry (including first and second switching circuits 250, 252). As shown, the second switching circuit may include a plurality of electronic components (e.g., resistors, diodes, capacitors, operational amplifiers, transistors and the like). In one example, as shown in FIG. 4, the second switching circuit may include a configuration of resistors R4, R5 and R6, diodes D1 and D2 (e.g., traditional diodes, or a zener diodes configured to implement a voltage shunt regulator), and a transistor Q1 (e.g., a metal-oxide-semiconductor field-effect transistor (MOSFET)) configured to receive and forward a signal to the heating element 220, as power directed thereto in an instance in which the signal has a voltage level above the predetermined threshold voltage, or receive and forward a signal to the authentication device 228 as one of the authentication signals in an instance in which the signal has a voltage level at or below the predetermined threshold voltage.

In another example, as shown in FIG. 5, the second switching circuit 252 may include a configuration of resistors R7, R8 and R9, capacitors C1, diodes D3 and D4 (e.g., a traditional diode or schottky diode), and a transistor Q1 (e.g., a MOSFET) configured to switch a PWM signal having a first frequency across the two-wire electrical connectors 246, 248 between pulses of a PWM signal having a second frequency where the first frequency is at least two times larger than the second frequency. It should be noted that although the implementation of FIGS. 4 and 5 are illustrated separately, the second switching circuit may include both configurations of the electronic components therein.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-7 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:

a cartridge that is equipped with a heating element and an authentication device, and contains an aerosol precursor composition; and a control body coupled with the cartridge and configured to exchange authentication signals with the authentication device to authenticate the cartridge for use with the control body, and only in instances in which the cartridge is authenticated, direct power to the heating element to activate and vaporize components of the aerosol precursor composition, wherein the control body and the cartridge include respectively a two-wire electrical connector and a corresponding two-wire electrical connector coupled with one another, and across which the authentication signals are exchanged and the power is directed, and wherein the control body and the cartridge further include respectively a first switching circuit and a second switching circuit, the first switching circuit being coupled with the second switching circuit to form switching circuitry configured to manage the authentication signals and the power across the two-wire electrical connector.

2. The aerosol delivery device of claim 1, wherein the authentication signals across the two-wire electrical connector have a voltage level at or below a predetermined threshold voltage, and the power across the two-wire electrical connector has a voltage level above the predetermined threshold voltage.

3. The aerosol delivery device of claim 2, wherein the predetermined threshold voltage is 2.5 volts.

4. The aerosol delivery device of claim 2, wherein the switching circuitry being configured to manage the authentication signals and the power across the two-wire electrical connector includes being configured to receive and forward a signal to the authentication device as one of the authentication signals in an instance in which the signal has a voltage level at or below the predetermined threshold voltage.

5. The aerosol delivery device of claim 4, wherein the switching circuitry being configured to receive and forward the signal includes being configured to receive a plurality of signals and forward signals of the plurality of signals to the authentication device as authentication signals until a signal of the plurality of signals has a voltage level above the predetermined threshold voltage.

6. The aerosol delivery device of claim 2, wherein the switching circuitry being configured to manage the authentication signals and the power across the two-wire electrical connector includes being configured to receive and forward a signal to the heating element as power directed thereto in an instance in which the signal has a voltage level above the predetermined threshold voltage.

7. The aerosol delivery device of claim 1, wherein the authentication signals and the power are formatted as pulse width modulation (PWM) signals having respectively a first frequency and a second frequency, the first frequency being at least two times larger than the second frequency.

8. The aerosol delivery device of claim 7, wherein the switching circuitry being configured to manage the authentication signals and the power across the two-wire electrical connector includes the switching circuitry being configured to switch a PWM signal having the first frequency across the two-wire electrical connector between pulses of a PWM signal having the second frequency.

9. The aerosol delivery device of claim 1, wherein the control component being configured to direct power to the heating element includes being configured to direct power to the heating element in response to a flow of air through at least a portion of the aerosol delivery device, the air being combinable with vapor formed by vaporization of components of the aerosol precursor composition to form an aerosol.

10. A control body coupleable with a cartridge that is equipped with a heating element and an authentication device, and contains an aerosol precursor composition, the control body being coupleable with the cartridge to form an aerosol delivery device, the control body comprising:

a control component configured to exchange authentication signals with the authentication device to authenticate the cartridge for use with the control body, and only in instances in which the cartridge is authenticated, direct power to the heating element to activate and vaporize components of the aerosol precursor composition;

a two-wire electrical connector coupled with a corresponding two-wire electrical connector of the cartridge when the control body is coupled with the cartridge, and across which the authentication signals are exchanged and the power is directed; and a first switching circuit coupled with a second switching circuit of the cartridge when the control body is coupled with the cartridge, the first switching circuit being coupled with the second switching circuit to form switching circuitry configured to manage the authentication signals and the power across the two-wire electrical connector.

11. The control body of claim 10, wherein the authentication signals across the two-wire electrical connector have a voltage level at or below a predetermined threshold voltage, and the power across the two-wire electrical connector has a voltage level above the predetermined threshold voltage.

12. The control body of claim 11, wherein the predetermined threshold voltage is 2.5 volts.

13. The control body of claim 11, wherein the switching circuitry being configured to manage the authentication signals and the power across the two-wire electrical connector includes being configured to receive and forward a signal to the authentication device as one of the authentication signals in an instance in which the signal has a voltage level at or below the predetermined threshold voltage.

14. The control body of claim 13, wherein the switching circuitry being configured to receive and forward the signal includes being configured to receive a plurality of signals and forward signals of the plurality of signals to the authentication device as authentication signals until a signal of the plurality of signals has a voltage level above the predetermined threshold voltage.

15. The control body of claim 11, wherein the switching circuitry being configured to manage the authentication signals and the power across the two-wire electrical connector includes being configured to receive and forward a signal to the heating element as power directed thereto in an instance in which the signal has a voltage level above the predetermined threshold voltage.

16. The control body of claim 10, wherein the authentication signals and the power are formatted as pulse width modulation (PWM) signals having respectively a first frequency and a second frequency, the first frequency being at least two times larger than the second frequency.

17. The control body of claim 16, wherein the switching circuitry being configured to manage the authentication signals and the power across the two-wire electrical connector includes the switching circuitry being configured to switch a PWM signal having the first frequency across the two-wire electrical connector between pulses of a PWM signal having the second frequency.

18. The control body of claim 10, wherein the control component being configured to direct power to the heating element includes being configured to direct power to the heating element in response to a flow of air through at least a portion of the aerosol delivery device, the air being combinable with vapor formed by vaporization of components of the aerosol precursor composition to form an aerosol.

* * * * *